US009253953B2

(12) United States Patent
Eggink et al.

(10) Patent No.: US 9,253,953 B2
(45) Date of Patent: Feb. 9, 2016

(54) FRUIT FORMATION IN THE ABSENCE OF FERTILISATION

(71) Applicant: RIJK ZWAAN ZAADTEELT EN ZAADHANDEL B.V., De Lier (NL)

(72) Inventors: Pieter Martijn Eggink, Oostvoorne (NL); Cornelis Maria Petrus Van Dun, Roosendaal (NL); Jacob Pieter Willem Haanstra, Dordrecht (NL)

(73) Assignee: RIJK ZWAAN ZAADTEELT EN ZAADHANDEL B.V, De Lier (NL)

( * ) Notice: Subject to any disclaimer, the term of this patent is extended or adjusted under 35 U.S.C. 154(b) by 528 days.

(21) Appl. No.: 13/774,622

(22) Filed: Feb. 22, 2013

(65) Prior Publication Data

US 2013/0239258 A1    Sep. 12, 2013

Related U.S. Application Data

(63) Continuation-in-part of application No. PCT/NL2011/050890, filed on Dec. 22, 2011.

(30) Foreign Application Priority Data

Dec. 22, 2010  (NL) ..................................... 2005908

(51) Int. Cl.
  *A01H 5/00* (2006.01)
  *A01H 5/08* (2006.01)
  *A01H 5/10* (2006.01)
  *C12N 5/02* (2006.01)
  *C12N 5/04* (2006.01)
  *A01H 1/06* (2006.01)
  *A23L 1/212* (2006.01)

(52) U.S. Cl.
  CPC .. *A01H 5/08* (2013.01); *A01H 1/06* (2013.01); *A23L 1/212* (2013.01)

(58) Field of Classification Search
  None
  See application file for complete search history.

(56) References Cited

U.S. PATENT DOCUMENTS

| 6,060,648 | A  | 5/2000  | Heath     |
| 8,492,619 | B2 | 7/2013  | Bar et al. |
| 8,957,286 | B2 | 2/2015  | Shirai    |
| 2010/0333228 | A1 | 12/2010 | Shirai |
| 2013/0145489 | A1 | 6/2013  | Gorguet et al. |
| 2013/0239258 | A1 | 9/2013  | Eggink et al. |
| 2013/0298292 | A1 | 11/2013 | Bar et al. |

FOREIGN PATENT DOCUMENTS

| EP | 1026942 | 8/2008 |
| EP | 2245922 A1 | 11/2010 |
| NL | 2005908 | 6/2012 |
| WO | 99/21411 | 5/1999 |
| WO | WO 2008/152134 | 12/2008 |
| WO | 2009/098983 | 8/2009 |
| WO | WO 2010/101274 | 9/2010 |
| WO | 2012/087140 | 6/2012 |
| WO | 2013/078319 | 5/2013 |

OTHER PUBLICATIONS

Talebi et al (American Journal of Plant Sciences, 3, pp. 1661-1665, 2012).*
Alcantara, T.P. et. al., "Ethyl methanesulfonate-induced seed mutagenesis of Capsicum annuum," Journal of Heredity, vol. 87, No. 3, 1996, pp. 239-241.
Ishikawa Keiko et. al., "High beta-carotene and capsaicinoid contents in seedless fruits of 'Shishiroh' pepper", Hortscience, American Societyof Horticultural Science, vol. 39, No. 1, Feb. 2004, pp. 153-155.
Anonymous: "Planet, F1", Mar. 31, 2010, XP002652088, Retrieved from the Internet: http://www.docstoc.com/docs/29159087/f [retrieved on Jul. 21, 2011].
Carolina Carrizo Garcia, "Fruit characteristics, seed production and pollen tube growth in the wild chilli pepper Capsicum flexuisum", Flora—Morphology, Distribution, Functional Ecology of Plants, Dec. 21, 2010, p. 339.
Charles, W.B. et. al., "Seedlessness in Capsicum-Annuum-Var-Longum", Journal of Horticulture Science, Headley Bros.Ltd Invicta Press, vol. 54, No. 2, Jan. 1979, p. 159-161.
Tiwari, A. Et. al., "Selection of Sweet Pepper (*Capsicum annuum* L.) Genotypes for Parthenocarpic Fruit Growth", Acta Horticulturae, vol. 761, Sep. 1, 2007, pp. 135-140.

* cited by examiner

*Primary Examiner* — Elizabeth McElwain
*Assistant Examiner* — Stephen Uyeno
(74) *Attorney, Agent, or Firm* — Vedder Price P.C.; Thomas J. Kowalski; Deborah L. Lu

(57) ABSTRACT

The present invention relates to a pepper plant showing the trait fruit formation in the absence of fertilization wherein said trait is obtainable by introgression from a plant grown from seed that was deposited with the NCIMB under accession number NCIMB 41678, NCIMB 41680, or NCIMB 41684. The invention further relates to progeny of the plant, propagation material for producing the plant, to fruits of the plant and to a food product comprising the fruit or parts thereof.

23 Claims, 1 Drawing Sheet

FRUIT FORMATION IN THE ABSENCE OF FERTILISATION

RELATED APPLICATIONS AND INCORPORATION BY REFERENCE

This application is a continuation-in-part application of international patent application Serial No. PCT/NL2011/050890 filed 22 Dec. 2011, which published as PCT Publication No. WO 2012/087140 on 28 Jun. 2012, which claims benefit of NL patent application Serial No. 2005908 filed 22 Dec. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to plants and plant parts, in particular fruity vegetables, which are altered with respect to their mode of fruit formation. More in particular, this invention relates to pepper plants that show fruit formation in the absence of fertilisation. This mode of fruit formation is often referred to as parthenocarpy and the fruits are called parthenocarpic fruits. The invention also relates to seeds of these plants capable of producing parthenocarpic fruits. The invention further relates to methods for obtaining said plants with altered genotypes and seeds thereof, which show fruit formation in the absence of fertilisation.

BACKGROUND OF THE INVENTION

Breeding of fruity vegetables like peppers aims at the production of commercial varieties optimally adapted to a professional production environment in order to produce marketable products. Many characteristics need to be taken into account during selection which relate to both input and output traits. One of the very important traits in this respect relates to fruit set, in particular to fruit set under unfavourable environmental conditions such as high or low temperatures and drought. Such conditions can be detrimental for normal pollination and thereby fertilisation, which leads to poor fruit set and as a consequence yield loss. When fruit formation in the absence of fertilisation or parthenocarpy can be harnessed as a trait, it is an important characteristic that can significantly contribute to an economically more efficient production of pepper fruits for several reasons.

In addition to contributing to harvest security, parthenocarpy is also important for fruit quality. Blossom-end rot (BER) is a physiological disorder caused by a local calcium deficiency during the initial stage of fruit development. BER is of economic importance since it causes high yield losses in pepper. The occurrence of BER is strongly correlated with a high initial growth rate, but also with the number of seeds in a fruit. Parthenocarpic peppers are reported to be less susceptible to BER since they do not contain any seeds (Heuvelink and Körner; Annals of Botany 88: 69-74, 2001).

Furthermore, industrial or domestic applications which require seed removal from the fruits can benefit strongly from parthenocarpy. In the food processing industry seeds are usually removed by washing the seeds away with water. Since this step is redundant for the processing of parthenocarpic peppers there are less processing costs involved. Also for domestic applications parthenocarpic fruits have advantages over seeded fruits, because it is easier for consumers to process the fruits due to the absence of seeds.

The formation of fruits in the absence of fertilisation gives rise to the possibility to combine this character with a genetic source of male sterility, in particular GMS (Genetic Male Sterility). This form of male sterility causes anthers not to develop, therefore no pollen are produced. This has several advantages for the grower. First of all, the undeveloped anthers will decrease the chances for personnel to develop allergic reactions to pollen. Secondly, a cost reduction can be made because bumblebees or other pollinators normally used to optimize fruit set are not necessary anymore, since fruits will set in the absence of fertilisation.

Another high valued trait of parthenocarpy is that it stabilizes the production flow of pepper fruits. Normally, the production of peppers is characterized by periods with high production of fruits alternated with periods with low production. This phenomenon in the pepper production chain is called flushing. This cyclic behaviour leads to periods with high supply and low prices and periods with a low supply and high prices. Avoiding this irregular yield pattern in the pepper production process and providing a more stable production of peppers is of great economic importance. The fluctuations in pepper production are mainly caused by fluctuations in fruit set. The presence of several developing fruits set at approximately the same time inhibit the fruit set and growth of new fruits because of competition for resources and dominance due to the production of plant growth regulators.

Furthermore, it is known that an increase in the number of seeds in a pepper also increases the inhibitory effect of a fruit on set and growth of later developing fruits. Hence, the fluctuations in pepper production will be less by growing parthenocarpic fruits, which do not contain seeds (Heuvelink and Korner; Annals of Botany 88: 69-74, 2001).

Fruit set normally depends on fertilisation. Fertilisation is the process in which both the egg cell and central cell contained within the ovule are fused with a sperm cell delivered by the pollen tube. This so-called double fertilisation is the step which triggers a cascade of events leading to the formation of the embryo and endosperm and finally to a mature seed. The developing seeds and surrounding tissues generate a signal which stimulates the outgrowth of the ovary and its development into a fleshy fruit. Apparently fertilisation lifts a certain developmental barrier which prevents fruit formation. This mechanism assures the fruit formation to be dependent on the formation of seeds which makes sense given the biological role of fruits in seed dispersal.

However, the knowledge of the physiological and molecular events which play a role in the initial steps of fruit formation is fragmentary. The involvement of the plant hormones auxin and gibberellin has been extensively documented although their precise role remains elusive. The application of either auxin or gibberellin to the unfertilised ovule leads in many plant species including pepper to fruit formation. In fact, these hormones are applied in practice to improve fruit set when greenhouse conditions are suboptimal. Although the application of auxin and gibberellin has some practical value it increases cost and it may lead to irregularities in fruit shape.

In addition to these exogenous effects, it is assumed that the hormones auxin and gibberellin also play a role during fertilisation dependent fruit formation although it is not clear which tissues are the actual source of these hormones. The hierarchy of these hormones as well as the downstream regulatory network is still largely unknown. Other hormones such as cytokinins, abscisic acid, ethylene and brassinosteroid also seem to play a role in fruit formation.

Most pepper genotypes exhibit a certain level of parthenocarpy. However, these parthenocarpic fruits show negative pleiotropic effects, such as a reduced fruit size, irregular and deformed shape of the fruit, and carpelloid growth inside the fruit (Tiwari et al. *BMC Plant Biology* 11:143, 2011). Carpelloid growth is the outgrowth of a pseudo-embryo inside a pepper fruit, which is a highly undesired effect for both grower and consumer. Parthenocarpic fruits showing negative pleiotropic effects are called knots and are not to be considered as real parthenocarpic fruits.

Given the significant advantages of parthenocarpy for the production of pepper fruits there is a strong need for a genetic source of parthenocarpy in pepper which allows the formation of fruits in absence of fertilisation, better known as parthenocarpic fruit formation, which is preferably not linked to negative pleiotropic effects.

Citation or identification of any document in this application is not an admission that such document is available as prior art to the present invention.

SUMMARY OF THE INVENTION

It is the object of the present invention to provide pepper plants which show fruit formation in the absence of fertilisation, without negative pleiotropic effects.

In the research leading to the present invention new pepper plants were developed by mutagenic treatment, showing fruit formation in the absence of fertilisation. It was surprisingly found that these plants formed parthenocarpic fruits having a size and shape similar to that of fruits formed after fertilisation.

The present invention thus provides pepper plants, which may comprise a genetic determinant which causes parthenocarpic fruit formation when homozygously present, wherein said determinant is obtainable by introgression from a plant grown from seed of which a representative sample was deposited with the NCIMB under accession number NCIMB 41678, NCIMB 41680, or NCIMB 41684.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with NCIMB, under deposit accession number 41678, 41680 and NCIMB 41684 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
FIG. 1: Appearance of harvested parthenocarpic pepper fruits, derived from NCIMB deposit 41684.
Figure 2:
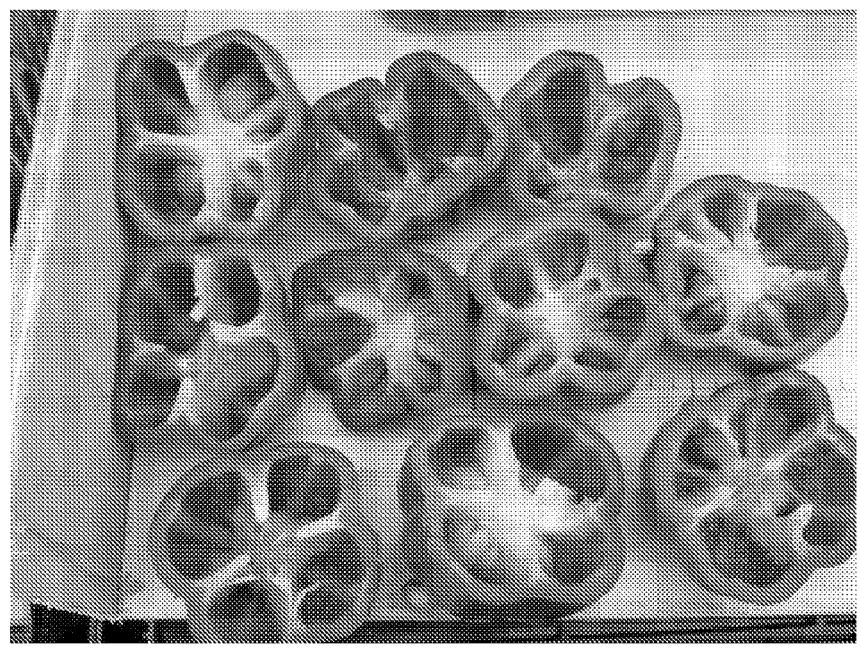
FIG. 2: Transverse section of the harvested parthenocarpic pepper fruits, obtained from plants derived from NCIMB deposit 41684.

Parthenocarpic fruits are fruits formed in the absence of fertilisation. Parthenocarpic fruit are therefore seedless fruits.

In one embodiment the parthenocarpic fruits produced by the plants of the invention are at least 80% seedless as compared to fruits formed after fertilisation.

In one embodiment the parthenocarpic fruits produced by the plants of the invention are at least 90% seedless as compared to fruits formed after fertilisation.

In one embodiment the parthenocarpic fruits produced by the plants of the invention are at least 95% seedless as compared to fruits formed after fertilisation.

In one embodiment the parthenocarpic fruits produced by the plants of the invention are at least 99% seedless as compared to fruits formed after fertilisation.

In one embodiment the parthenocarpic fruits produced by the plants of the invention are 100% seedless as compared to fruits formed after fertilisation.

The parthenocarpic fruits of the invention have an average length between about 87% and about 135%, preferably between about 90% and about 128%, more preferably between about 93% and about 121%, even more preferably between about 96% and about 107% and most preferably about 100% of that of a seeded fruit of the same plant or a plant with a similar or the same genetic background. The same genetic background in this respect means originating from the same cross.

In one embodiment the parthenocarpic fruits produced by the plants of the invention have an average length of at least about 87% as compared to fruits formed after fertilisation.

In one embodiment the parthenocarpic fruits produced by the plants of the invention have an average length of at least about 90% as compared to fruits formed after fertilisation.

In one embodiment the parthenocarpic fruits produced by the plants of the invention have an average length of at least about 93% as compared to fruits formed after fertilisation.

In one embodiment the parthenocarpic fruits produced by the plants of the invention have an average length of at least about 96% as compared to fruits formed after fertilisation.

In one embodiment the parthenocarpic fruits produced by the plants of the invention have an average length of at least about 100% as compared to fruits formed after fertilisation.

In one embodiment the parthenocarpic fruits produced by the plants of the invention have an average length of at least about 107% as compared to fruits formed after fertilisation.

In one embodiment the parthenocarpic fruits produced by the plants of the invention have an average length of at least about 114% as compared to fruits formed after fertilisation.

In one embodiment the parthenocarpic fruits produced by the plants of the invention have an average length of at least about 121% as compared to fruits formed after fertilisation.

In one embodiment the parthenocarpic fruits produced by the plants of the invention have an average length of at least about 128% as compared to fruits formed after fertilisation.

In one embodiment the parthenocarpic fruits produced by the plants of the invention have an average length of at least about 135% as compared to fruits formed after fertilisation.

In one embodiment the parthenocarpic fruits produced by the plants of the invention have an average length of about 150% as compared to fruits formed after fertilisation.

The width of the parthenocarpic fruits of the invention suitably varies between about 90% and about 110% of the width of fruits formed after fertilization. Preferably, the width varies between about 95% and about 105%, more preferably the width is between about 99% and 101%, most preferably the width is the same as in seeded fruits, i.e. 100% as compared to fruits formed after fertilization.

In one embodiment, the parthenocarpic fruits produced by the plants of the invention have an average width of at least about 90% as compared to fruits formed after fertilisation.

In another embodiment, the average width of fruits of the invention is at least about 95% of the fruits formed after fertilisation.

In another embodiment, the average width of fruits of the invention is at least about 99% of the fruits formed after fertilisation.

In a further embodiment, the average width of fruits of the invention is at least about 100% of the fruits formed after fertilisation.

In another embodiment, the average width of fruits of the invention is at least about 110% of the fruits formed after fertilisation.

In one embodiment, the invention relates to a pepper plant, wherein the genetic determinant leading to the parthenocarpic fruit formation of the invention is introgressed from a plant grown from seed of which a representative sample was deposited with the NCIMB under accession number NCIMB 41678, NCIMB 41680, or NCIMB 41684.

It should be noted that if the selection criterion or criteria is or are clearly defined, the skilled person will be able to identify the descendants that carry the trait that is the result of the genetic determinant of the invention in any further generation. For the trait of the invention descendants from a cross between a plant not carrying the parthenocarpic fruit formation trait and a plant carrying the parthenocarpic fruit formation trait of which representative seed was deposited under accession numbers NCIMB 41678, NCIMB 41680, or NCIMB 41684 that carry that trait may be found by growing F2 plants from seeds that are the result from the initial cross and a selfing step, preventing pollination of the plants thus obtained and selecting plants producing fruits as plants showing parthenocarpic fruit formation.

In one embodiment, plants carrying the genetic determinant and the phenotypic trait of the invention are obtainable from the deposit by:
(a) growing plants from seeds of which a representative sample was deposited under NCIMB numbers NCIMB 41678, NCIMB 41680 or NCIMB 41684;
(b) preventing pollination of the plants;
(c) selecting plants producing fruits as plants showing parthenocarpic fruit formation.

In one embodiment, the invention relates to a pepper plant, showing the trait parthenocarpic fruit formation, which plant is obtainable by:
(a) growing plants from seed of which a representative sample was deposited with the NCIMB under accession number NCIMB 41678, NCIMB 41680 or NCIMB 41684;
(b) preventing pollination of the plants;
(c) selecting plants producing fruits as plants showing parthenocarpic fruit formation;
(d) crossing a plant selected in step c) with a plant not carrying the genetic determinant to obtain a F1 population;
(e) selfing plants from the F1 to obtain a F2 population; and
(f) repeating steps b) and c) to identify plants showing parthenocarpic fruit formation.

Preventing pollination is suitably done by using a male sterile plant in step a).

Seeds of three representative pepper mutants were deposited on 19 Nov. 2009 and 25 Nov. 2010 with NCIMB Ltd. (Ferguson Building, Craibstone Estate, Bucksburn, Aberdeen, AB21 9YA). Table 1 shows the deposit accession numbers.

In one embodiment, the invention relates to a pepper plant, wherein the parthenocarpic fruit formation trait is obtainable from the (hybrid) pepper plant selected from hybrid plants grown from seeds of which a representative sample was deposited with NCIMB as listed in Table 1.

The trait in all three events is transferred in a pattern consistent with recessive inheritance, and selection for plants that carry the trait and genetic determinant of the invention is thus suitably made in the second generation (F2) after having selfed the F1.

In one embodiment, the invention further relates to a pepper plant showing the trait parthenocarpic fruit formation caused by a genetic determinant, wherein when said plant is homozygous for said determinant and said plant homozygous for said determinant is crossed with a tester plant homozygous for the said determinant, plants of the first generation progeny resulting from said cross show a 1:0 segregation for the trait parthenocarpic fruit formation.

In one embodiment, when said plants of said first generation progeny are self-pollinated, plants of the resulting second generation progeny show a 1:0 segregation for the trait parthenocarpic fruit formation. In one embodiment, the tester plant is a plant derived from any one of the mutant lines of which a representative sample of seed was deposited with NCIMB as listed in Table 1 and showing the trait parthenocarpic fruit formation, or a progeny plant showing the said trait as is present in any one of the mutant lines listed in Table 1.

In one embodiment, the tester plant is a plant of any one of the mutant lines of which a representative sample was deposited with NCIMB as listed in Table 1, or a progeny of said mutant lines showing the trait parthenocarpic fruit formation.

In one embodiment of the invention pollination is prevented by emasculating the flowers.

In another embodiment of the invention pollination is prevented by using a pepper plant grown from seeds of which a representative sample was deposited under the accession numbers listed in Table 1, which is male sterile.

In one embodiment, the parthenocarpic fruits of a pepper of the invention have a similar number of incidences of carpelloid outgrowths as compared to fruits obtained after fertilisation of the same plant or a near isogenic control plant.

In one embodiment, the parthenocarpic fruits of a pepper of the invention have less incidences of carpelloid outgrowths as compared to fruits obtained after fertilisation of the same plant or a near isogenic control plant.

In one embodiment, the pepper plants of the invention and the fruits thereof do essentially not show any negative pleiotropic effects. The fruits are seedless and are in terms of their size, shape, and incidences of carpelloid outgrowths comparable to fruits obtained after fertilization of the same plant or a near isogenic control plant.

In one embodiment, the phenotypic expression of the genetic trait of the invention may comprise not only the formation of fruits in the absence of fertilisation but also the formation of fruits that have a size and/or shape comparable to that of fruits formed after fertilisation and/or have similar incidences of carpelloid outgrowths. In one embodiment, the combined expression of these phenotypic characteristics is typical for the trait of the invention.

In one embodiment, the invention relates to the fruits produced by the pepper plants of the invention and parts thereof.

TABLE 1

Deposit accession numbers of parthenocarpic pepper mutants.

| Name | Mutant number (internal designation) | NCIMB number |
| --- | --- | --- |
| Capsicum annuum | 09R.6351-M | NCIMB 41678 |
| Capsicum annuum | 09R.6367-M | NCIMB 41680 |
| Capsicum annuum | 09R.6401-M | NCIMB 41684 |

The mutants were deposited on 19 Nov. 2009 with NCIMB Ltd., Ferguson Building, Craibstone Estate, Bucksburn, Aberdeen, AB21 9YA Scotland, UK.

The pepper plants according to the invention may grow the following fruit types: a sweet pepper including a dolce-type pepper, a bell pepper, a big rectangular pepper, a conical pepper, a long conical pepper or a blocky-type pepper.

The fruits of the pepper plants according to the invention at maturity may be a green, yellow, orange, red, ivory, brown, or purple fruit.

In one embodiment, the pepper plant of the invention is a representative of one of the following species: *Capsicum annuum, Capsicum baccatum, Capsicum chacoense, Capsicum chinense, Capsicum frutescens*, or any hybrid combination thereof. These species are the most commonly used breeds and in addition may easily be crossed amongst each other, thus facilitating obtaining a plant showing the parthenocarpic trait of the invention.

The invention further relates to seed of the pepper plants of the invention and to other parts of the plant that are suitable for sexual reproduction, i.e. propagation material. Such parts are for example selected from the group consisting of microspores, pollen, ovaries, ovules, embryo sacs and egg cells. The seeds carry the genetic determinant that causes the trait of parthenocarpic fruit formation, either in homozygous or heterozygous form.

In addition, the invention relates to parts of the plant that are suitable for vegetative reproduction, in particular cuttings, roots, stems, cells, protoplasts, and tissue culture of the pepper plants of the invention. The tissue culture may comprise regenerable cells. Such a tissue culture may be derived from leaves, pollen, embryos, cotyledon, hypocotyls, meristematic cells, roots, root tips, anthers, flowers, seeds and stems. The propagation material carries the genetic determinant that causes the trait of parthenocarpic fruit formation, either in homozygous or heterozygous form.

The invention also relates to progeny of the pepper plants of the invention. Such progeny may be produced by sexual or vegetative reproduction of a plant of the invention or a progeny plant thereof. The progeny carries the genetic determinant that causes the trait of parthenocarpic fruit formation, either in homozygous or heterozygous form. When the determinant is homozygously present, the progeny plant grows fruits independent of fertilisation in the same or a similar way as one of the plants, of which representative seed was deposited (Table 1). This means that such progeny has the same characteristics as claimed for the pepper plants of the invention. In addition to this, the plant may be modified in one or more other characteristics. Such additional modifications are for example effected by mutagenesis or by transformation with a transgene.

The invention, furthermore, relates to hybrid seed and to a method of producing hybrid seed which may comprise crossing a first parent plant with a second parent plant and harvesting the resultant hybrid seed. In case the trait is recessive, both parent plants need to be homozygous for the parthenocarpy trait in order for the hybrid seed to carry the trait of the invention. They need not necessarily be uniform for other traits. Both parents thus carry the genetic determinant in homozygous form.

It is clear that a parent that provides the trait and genetic determinant of the invention is not necessarily a plant grown directly from the deposited seeds. The parent may also be a progeny plant from the seed or a progeny plant from seeds that are identified to have or to have acquired the genetic determinant causing the trait of the invention by other means.

In one embodiment, the invention relates to pepper plants that carry the genetic determinant causing the trait of the invention and having acquired said genetic determinant by introduction of the genetic information that is responsible for the trait from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the genetic information, in particular the genetic determinant, is acquired is formed by plants grown from the deposited seeds or sexual or vegetative descendants thereof.

The invention also relates to the germplasm of plants of the invention. The germplasm is constituted by all inherited characteristics of an organism and according to the invention encompasses at least the parthenocarpy trait of the invention.

The invention further relates to cells of the pepper plants that show the fruit formation in the absence of fertilisation. Each cell of such pepper plants carries the genetic information, in particular the genetic determinant, that leads to phenotypic expression of said trait. The cell may be an individual cell or be part of a pepper plant or pepper plant part.

The invention also relates to the parthenocarpic pepper fruits that are produced by the plants of the invention. In addition, the invention relates to parts of the pepper fruits and processed products produced from the pepper fruits.

In one embodiment, the invention relates to a method for production of a pepper plant which may comprise a genetic determinant which causes parthenocarpic fruit formation, which may comprise:
(a) crossing a plant which may comprise the genetic determinant that leads to parthenocarpic fruit formation with another plant;
(b) selfing the resulting F1 to obtain an F2;
(c) selecting for resistant plants in the F2;
(d) optionally performing one or more additional rounds of selfing or crossing, and subsequently selecting, for a plant producing parthenocarpic fruits.

In one embodiment, the invention relates to a method for production of a pepper plant which may comprise a genetic determinant which causes parthenocarpic fruit formation, which may comprise:
(a) crossing a plant which may comprise the genetic determinant that leads to parthenocarpic fruit formation with another plant;
(b) optionally backcrossing the resulting F1 with the preferred parent;
(c) selecting for resistant plants in the F2;
(d) optionally performing one or more additional rounds of selfing or crossing, and subsequently selecting, for a plant producing parthenocarpic fruits.

The invention additionally provides a method of introducing a desired trait into a pepper plant that produces parthenocarpic fruits, which may comprise:
(a) crossing a pepper plant which may comprise a genetic determinant that causes the plant to produce parthenocarpic fruits, representative seed of which plant were deposited with the NCIMB under deposit number NCIMB NCIMB 41678, NCIMB 41680, or NCIMB 41684 with a second pepper plant that may comprise a desired trait to produce F1 progeny;
(b) selecting F1 progeny that produces parthenocarpic fruits and expresses the desired trait;
(c) crossing the selected F1 progeny with either parent, to produce backcross progeny;
(d) selecting backcross progeny which may comprise the desired trait and the parthenocarpic fruit formation; and
(e) optionally repeating steps (c) and (d) one or more times in succession to produce selected fourth or higher backcross progeny that may comprise the desired trait and produces parthenocarpic fruits. The invention, of course, includes a pepper plant produced by this method. The parthenocarpic fruit formation is suitably caused by the genetic determinant that is present in plants grown from the deposited seeds and leads in these plants to parthenocarpic fruit formation.

In one embodiment selection for resistant plants is done in the F1.

In one embodiment selection for resistant plants is started in the F3 or a later generation.

In one embodiment the plant which may comprise the genetic determinant is a plant of an inbred line, a hybrid, a doubled haploid, or of a segregating population.

In one embodiment, the invention relates to a method for the production of a pepper plant producing parthenocarpic fruits by using a doubled haploid generation technique to generate a doubled haploid line which may comprise the said trait and genetic determinant causing the trait.

In one embodiment, the invention relates to a method for producing a hybrid pepper plant which may comprise crossing a first parent pepper plant with a second parent pepper plant and harvesting the resultant hybrid pepper seed, in which the first parent pepper plant and/or the second parent pepper plant produce parthenocarpic fruits as a result of the presence in their genome of the genetic determinant as found in the deposited seeds.

The invention also relates to a method for the production of a pepper plant producing parthenocarpic fruits by using a seed that may comprise in its genome the genetic determinant that causes the parthenocarpic fruit formation and that is also found in the genome of the deposited seeds for growing the said pepper plant.

The invention also relates to a method for seed production which may comprise growing plants from seeds of which a representative sample was deposited with the NCIMB under deposit number NCIMB 41678, NCIMB 41680, or NCIMB 41684, allowing the plants to produce seeds, and harvesting those seeds. Production of the seeds is suitably done by crossing or selfing.

In one embodiment, the invention relates to a method for the production of a pepper plant that produces parthenocarpic fruits according to the invention by using tissue culture. The invention furthermore relates to a method for the production of a pepper plant that produces parthenocarpic fruits according to the invention by using vegetative reproduction.

In one embodiment, the invention relates to a method for the production of a pepper plant that produces parthenocarpic fruits according to the invention by using a method for genetic modification to introduce the resistance into the pepper plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant. According to a further aspect of the invention the gene underlying the parthenocarpy trait of the invention as present in the deposited seeds is introduced by genetic modification in an acceptor plant.

The invention relates to a method for the production of a parthenocarpic pepper plant, wherein progeny or propagation material of a plant which may comprise the genetic determinant conferring said parthenocarpy trait is used as a source to introgress the parthenocarpy trait into another plant.

The invention also relates to the germplasm of plants of the invention. The germplasm is constituted by all inherited characteristics of an organism and according to the invention encompasses at least the parthenocarpy trait of the invention. The germplasm may be used in a breeding program for the development of pepper plants that produce parthenocarpic fruits.

The invention also relates to a breeding method for the development of pepper plants that produce parthenocarpic fruits wherein germplasm which may comprise a genetic determinant causing the production of fruits in the absence of fertilization is used.

Representative seed of plants that are used as a parent or source in the above described methods and that comprise the genetic determinant was deposited with the NCIMB under deposit number NCIMB 41678, NCIMB 41680 and NCIMB 41684.

A "seeded fruit" is a normal fruit containing seeds, which will only be formed after fertilisation of the female gamete has occurred.

A "knot" is a seedless fruit produced in the absence of fertilisation. Such a fruit typically has an aberrant appearance compared to a fruit of the same plant that has formed after fertilisation. A knot usually has a length of less than 84% of that of a normal fruit, containing seeds. Furthermore, the weight of a seedless knot is usually lower than that of a fruit formed after fertilisation (Tiwari et al., Proc. XXVII IHC-S6 High-Qual. Crop Prod. Under Protect. Cultiv., Acta Hort. 761, ISHS (2007)). Also a knot usually has more ribs when compared to a fruit formed after fertilisation. A knot usually does not have a marketable value.

A "parthenocarpic fruit" is formed in the absence of fertilisation. However, unlike a knot a parthenocarpic fruit does not have an aberrant appearance and resembles a seeded fruit.

"Parthenocarpy" is the formation of seedless fruits having a similar appearance as seeded fruits, in the absence of fertilisation. A plant is considered to have the genetic determinant that leads to the production of parthenocarpic fruits according to the invention when at least one, preferably two, more preferably three, even more preferably four and most preferably all of the following criteria are met:

(a) 10 randomly picked parthenocarpic fruits of two fruit sets comply at least with the US standard classification class Fancy (US Fancy);
(b) the 10 randomly picked parthenocarpic fruits have an average length of at least about 90% of that of 10 randomly picked seeded fruits of two fruit sets of a plant with the same genetic background, preferably of the same plant;
(c) the 10 randomly picked parthenocarpic fruits have an average width of at least about 90% of that of 10 randomly picked seeded fruits of two fruit sets of a plant with the same genetic background, preferably of the same plant;
(d) the 10 randomly picked parthenocarpic fruits show the same or similar degree of uniformity as 10 randomly picked seeded fruits of two fruit sets of a plant with a similar genetic background, preferably of the same plant;
(e) the 10 randomly picked parthenocarpic fruits preferably show a similar number of incidences of carpelloid outgrowths as 10 randomly picked seeded fruits of two fruit sets of a plant with a similar genetic background, preferably of the same plant.

The grade "US Fancy" consists of mature sweet peppers of a specified color, which are firm, well shaped, and free from Blossom End Rot, crushed/broken, freezing, freezing injury, hail, insects, mechanical, sunscald, decay affecting calyxes and/or walls, decay affecting stems, and from injury caused by bruising, dirt, discoloration, disease, insects, pitting, scars, shriveling, sunburn, or other means. At least 90% of the peppers show any amount of the specified color.

"Uniformity" means having similar deviations in shape and size as the comparison. This also means that when within the group of ten randomly picked fruits some of the fruits are essentially different in shape or size, the control group should have similar deviations.

"Introgression" as used in this application is intended to mean introduction of a trait from a donor plant into a plant not carrying the genetic determinant causing the trait (acceptor plant) by means of conventional crossing and selection at least for the number of generations needed to bestow the trait upon the acceptor plant or transfer the genetic determinant to the genome of the acceptor plant.

"Progeny" as used in this application is intended to mean the first and all further descendants from a cross with a plant of the invention that shows fruit formation in the absence of fertilisation. Progeny of the invention are descendants of any cross with a plant of the invention that carries the trait that leads to fruit formation in the absence of fertilisation and the genetic determinant causing the trait.

"Progeny" also encompasses plants that carry the genetic determinant that when homozygously present causes the trait of parthenocarpic fruit formation of the invention and are obtained from other plants of the invention by vegetative propagation or multiplication.

Progeny is not only the first but also all further generations as long as the parthenocarpy trait and/or the genetic determinant causing it are retained. Progeny typically has an ancestor that is a plant having the ability to develop fruits independently from fertilisation as is found in plants from seed as deposited. An ancestor is intended to encompass not only the generation immediately prior to the plant but also multiple generations before that. More in particular, the ancestor is a plant from the deposited seed or a further generation descendent therefrom.

EXAMPLES

Example 1

Genetic Modification of Pepper by Ethyl Methane Sulfonate (EMS)

Seeds of a hybrid red blocky pepper (RZ N02.52) which are heterozygous for the recessive trait of male sterility were treated with ems by submergence of approximately 10,000 seeds into an aerated solution of 0.5% (w/v) ems during 24 hours at room temperature.

The treated seeds were germinated and the resulting plants were grown in a greenhouse to produce M2 seeds.

After maturation, M2 seeds were harvested and bulked in one pool. The resulting pool of M2 seeds was used as starting material to identify the individual M2 plants showing fruit formation in the absence of fertilisation.

The efficacy of the genetic modification procedure was assessed by determining the occurrence of bleached plants, which is indicative for chlorophyll loss due to modifications in genes directly or indirectly involved in the formation or accumulation of chlorophyll.

Example 2

Identification of Pepper Plants which have Obtained the Trait of Fruit Formation in the Absence of Fertilization 100,000 M2 pepper seeds were sown in soil and grown to small plantlets. Subsequently, approximately 86,000 plants were transferred to tunnel greenhouses in which they were raised according to common pepper cultivation practice. Approximately 12,000 plants were male sterile.

These plants were monitored on a regular basis in order to determine which mutants show fruit formation in the absence of fertilisation. As first selection criteria were used the formation of fruits of a size and shape similar to that of normal seeded fruits of not mutated pepper plants of RZ 02-52. Subsequently, from the selected plants those were selected which produced seedless fruits and which showed similar or less incidences of carpelloid outgrowths as seeded fruits of the not mutated plants of RZ 02-52. On the basis of these criteria three parthenocarpic mutants were selected as the best events.

Example 3

Heritability of the Parthenocarpy Trait

F1 seeds were produced by crossing the three selected parthenocarpic mutants with a line which was heterozygous for the recessive trait of male sterility. Per F1 population a total of 8 plants of which 4 were male sterile were grown in the greenhouse according to common pepper cultivation practice.

The male sterile plants of each population were monitored for parthenocarpic fruit formation. It was observed that none of the male sterile plants showed parthenocarpic fruit formation. The fertile F1 plants were selfed in order to obtain an F2 population. The male sterile plants were again monitored for parthenocarpic fruit formation. It was observed that approximately 25% of the plants of the F2 populations derived from the three selected mutants showed parthenocarpic fruit formation. In Tables 2 and 3, examples of selected parthenocarpic F2 plants are given. Each deposit is an F3 batch of seeds coming from 4 fertile (heterozygous for male sterility) F2 plants indicated in Tables 2 and 3. The deposits are heterozygous for male sterility.

TABLE 2

| Accession | Average length fruit set 1 (5 fruits) | Average length fruit set 2 (5 fruits) | Average length Set 1 + 2 (10 fruits) | length compared to seeded control |
|---|---|---|---|---|
| 6350-3 F2 | 8.6 | 8.7 | 8.65 | 1.20 |
| 6351 seeded | 6.8 | 7.6 | 7.2 | 1.00 |
| 6366-3 F2 | 7.8 | 7.2 | 7.5 | 0.94 |
| 6367 seeded | 8.4 | 7.5 | 7.95 | 1.00 |
| 6400-4 F2 | 8.2 | 8.3 | 8.25 | 1.25 |
| 6401 seeded | 6.6 | 6.6 | 6.6 | 1.00 |
| Control (knots) line A sterile | 5.2 | 6.6 | 5.9 | 0.84 |
| Control (seeded) line A fertile | 6.6 | 7.4 | 7.0 | 1.00 |

TABLE 3

| Accession | Average width fruit set 1 (5 fruits) | Average width fruit set 2 (5 fruits) | Average width Set 1 + 2 (10 fruits) | Width compared to seeded control |
|---|---|---|---|---|
| 6350-3 F2 | 7.3 | 7.6 | 7.45 | 0.90 |
| 6351 seeded | 8.6 | 8.0 | 8.2 | 1.00 |
| 6365-3 F2 | 8.8 | 8.2 | 8.5 | 0.95 |
| 6367 Seeded | 9 | 8.9 | 8.95 | 1.00 |
| 6400-4 F2 | 9 | 8.9 | 8.95 | 0.99 |
| 6401 seeded | 8.8 | 9.3 | 8.95 | 1.00 |
| Control (knots) line A sterile | 7.4 | 7.4 | 7.4 | 0.87 |
| Control (seeded) line A fertile | 8.3 | 8.8 | 8.55 | 1.00 |

To confirm segregation of the trait parthenocarpic fruit formation F3 populations for each event were checked. It was confirmed that in the F3 population of mutants 09R.6351-M (NCIMB 41678) and 09R.6367-M (NCIMB 41680) 4 out of 11 plants produced parthenocarpic fruits that have a length of at least 87% of the length of a seeded fruit and a width of at least 90% of the width of a seeded fruit (shaded boxes). For mutant 09R.6401-M (NCIMB 41684) this was 4 out of 12 plants (Table 4).

TABLE 4

| deposit | % length/fertile ratio S/gemF | % width/fertile ratio S/gemF |
|---|---|---|
| 6351-M | | |
| 6281-1 | 0.95 | 0.90 |
| 6281-2 | N.O. | N.O. |
| 6281-3 | 0.87 | 0.89 |
| 6281-4 | 0.97 | 0.77 |
| 6581-5 | 0.91 | 1.03 |
| 6281-6 | 0.80 | 1.04 |
| 6281-7 | 0.92 | 0.97 |
| 6281-8 | 0.77 | 0.91 |
| 6281-9 | 0.83 | 0.78 |
| 6281-10 | 0.93 | 1.12 |
| 6281-11 | 0.82 | 0.92 |
| 6281-12 | 0.94 | 0.83 |
| 6367-M | | |
| 6287-1 | N.O. | N.O. |
| 6287-2 | 0.92 | 0.91 |
| 6287-3 | 0.86 | 0.96 |
| 6287-4 | 1.04 | 0.91 |
| 6287-5 | 0.95 | 0.83 |
| 6287-6 | 0.92 | 0.90 |
| 6287-7 | 0.85 | 0.84 |
| 6287-8 | 0.98 | 0.87 |
| 6287-9 | 1.05 | 0.91 |
| 6287-10 | 0.87 | 0.89 |
| 6287-11 | 0.94 | 0.86 |
| 6287-12 | 0.98 | 0.83 |
| 6401-M | | |
| 6291-1 | 0.93 | 0.79 |
| 6291-2 | 0.92 | 0.72 |
| 6291-3 | 1.03 | 0.96 |
| 6291-4 | 0.88 | 0.71 |
| 6291-5 | 0.96 | 0.98 |
| 6291-6 | 1.00 | 0.84 |
| 6291-7 | 0.93 | 0.89 |
| 6291-8 | 0.96 | 0.80 |
| 6291-9 | 0.88 | 1.08 |
| 6291-10 | 0.95 | 0.77 |
| 6291-11 | 0.94 | 0.85 |
| 6291-12 | 0.99 | 0.96 |

"N.O." means no observation made

This shows that the parthenocarpic trait identified by the method given by this invention has a genetic basis. The trait in all three events is transferred in a pattern consistent with recessive inheritance.

Example 4

Transfer of the Parthenocarpic Fruit Formation Trait to Other Pepper Plants

To demonstrate that the parthenocarpic fruit formation trait of the invention can be introduced into other pepper types as well, crosses were made with various other pepper lines. In the F2, after having selfed the F1 plant, about 25% of the plants were found which produced seedless fruits, from flowers in which pollination was prevented, which are similar in appearance and other characteristics as compared to fruits grown from fertilized flowers of the same plant.

Example 5

Trait Analysis Test

In order to confirm which progeny plants of the three F2 populations as described in example 3 have the parthenocarpic fruit formation trait of the invention the average length of at least 10 fruits of the first two fruit sets of each sterile progeny plant was determined (Table 2).

As a comparison the average length of 10 fruits per plant of the two first fruits sets of 4 fertile plants from the same genetic background (F2) was determined (Table 2). These are normal fruits containing seeds.

As a second comparison, the average lengths of ten seedless fruits from the first two fruit sets of at least 4 plants producing knots were determined and compared to seeded fruits from at least 4 plants with the same genetic background. In this case the control (line A) was chosen in such a way that it is a representative commercial blocky pepper line with average fruit set under sterile conditions.

Progeny plants having seedless fruits with an average fruit length of at least 87% or more compared to the average fruit length of the seeded fruits of the control plant, are considered to be plants carrying the trait of the invention. In table 2 measurements are shown of individual F2 plants from example 4 which exhibit the trait of the invention.

The invention is further described by the following numbered paragraphs:

1. A pepper plant comprising a genetic determinant which causes parthenocarpic fruit formation when homozygously present, wherein said determinant is obtainable by introgression from a plant grown from seed that was deposited with the NCIMB under accession number NCIMB 41678, NCIMB 41680, or NCIMB 41684.

2. A pepper plant of paragraph 1, wherein the genetic determinant is introgressed from a plant grown from seed that was deposited with the NCIMB under accession number NCIMB 41678, NCIMB 41680, or NCIMB 41684.

3. A pepper plant of paragraph 1 or 2, obtainable by:
  a) growing plants from seed that was deposited with the NCIMB under accession number NCIMB 41678, NCIMB 41680, or NCIMB 41684;
  b) preventing pollination of the plants;
  c) selecting plants producing fruits as plants showing parthenocarpic fruit formation;
  d) crossing a plant selected in step c) with a plant not carrying the genetic determinant to obtain a F1 population;
  e) selfing plants from the F1 to obtain a F2 population; and
  f) repeating steps b) and c) to identify plants showing parthenocarpic fruit formation.

4. A pepper plant of paragraph 3, wherein pollination is prevented by emasculating the flowers.

5. A pepper plant of paragraph 3, wherein pollination is prevented by using a pepper plant in step a) which is male sterile.

6. A pepper plant of any one of paragraphs 1-5, wherein the parthenocarpic fruits have a size and/or shape similar to that of fruits formed after fertilisation.

7. Progeny of a pepper plant of paragraphs 1-6, wherein the progeny plant is capable of parthenocarpic fruit formation.

8. A pepper plant of any one of paragraphs 1-7, wherein the mature fruit of the plant is green, yellow, orange, red, ivory, brown, or purple.

9. A pepper plant of any one of paragraphs 1-7, wherein the mature fruit of the plant is either a sweet pepper including a dolce-type pepper, a bell pepper, a big rectangular pepper, a conical pepper, a long conical pepper or a blocky-type pepper.

10. A pepper plant of any one of paragraphs 1-7, wherein the pepper plant is a plant from the species *Capsicum annuum*, *Capsicum baccatum*, *Capsicum chacoense*, *Capsicum chinense*, *Capsicum frutescens*.

11. A pepper plant of any one of paragraphs 1-9, wherein the pepper plant is a hybrid.

12. Seed capable of growing into the plant of any one of paragraphs 1-11.

13. A parthenocarpic pepper fruit of a plant of any one of paragraphs 1-11, or of a plant grown from a seed of paragraph 12.

14. Pepper fruit of paragraph 13, wherein the fruit is at least 90% seedless, preferably at least 95% seedless, more preferably at least 98% seedless, even more preferably at least 99% seedless, most preferably 100% seedless.

15. Propagation material capable of growing into a plant of any of paragraphs 1-11.

16. Propagation material derived from a plant of any of paragraphs 1-11, wherein the propagation material comprises the genetic determinant as defined in paragraph 1.

17. Propagation material of paragraph 15 or 16, wherein the propagation material is selected from the group consisting of microspores, pollen, ovaries, ovules, embryos, embryo sacs, egg cells, cuttings, roots, root tips, hypocotyls, cotyledons, stems, leaves, flowers, anthers, seeds, meristematic cells, protoplasts, and cells.

18. Tissue culture of propagation material of any one of paragraphs 15-17.

19. Food product comprising a fruit or parts thereof of paragraph 13 or 14, optionally in processed form.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Capsicum annuum* pepper plant having a genetic background comprising a genetic determinant which causes parthenocarpic fruit formation when homozygously present,
  wherein said genetic determinant is as found in a plant grown from seed that was deposited with the NCIMB under accession number NCIMB 41678, NCIMB 41680, or NCIMB 41684 and
  wherein the parthenocarpic fruits have a size and/or shape similar to that of fruits formed after fertilisation.

2. The pepper plant as claimed in claim 1, obtained by:
  a) growing plants from seed that was deposited with the NCIMB under accession number NCIMB 41678, NCIMB 41680, or NCIMB 41684;
  b) preventing pollination of the plants;
  c) selecting plants producing fruits as plants showing parthenocarpic fruit formation;
  d) crossing a plant selected in step c) with a plant not carrying the genetic determinant to obtain a F1 population;
  e) selfing plants from the F1 to obtain a F2 population; and
  f) repeating steps b) and c) to identify plants showing parthenocarpic fruit formation.

3. The pepper plant as claimed in claim 2, wherein pollination is prevented by emasculating the flowers.

4. The pepper plant as claimed in claim 2, wherein pollination is prevented by using a pepper plant in step a) which is male sterile.

5. A progeny of a pepper plant as claimed in claim 1, comprising the genetic determinant.

6. The pepper plant as claimed in claim 1, wherein the mature fruit of the plant is green, yellow, orange, red, ivory, brown, or purple.

7. The pepper plant as claimed in claim 1, wherein the mature fruit of the plant is a dolce-type pepper, a bell pepper, a big rectangular pepper, a conical pepper, a long conical pepper or a blocky-type pepper.

8. The pepper plant as claimed in claim 1, wherein the pepper plant is a hybrid.

9. A seed capable of growing into the plant as claimed in claim 1, wherein said seed comprises said genetic determinant.

10. A parthenocarpic pepper fruit of a plant as claimed in claim 1, or of a plant grown from a seed as claimed in claim 9.

11. The parthenocarpic pepper fruit as claimed in claim 10, wherein the parthenocarpic fruit is at least 90% seedless.

12. A propagation material capable of growing into a plant as claimed in claim 1, wherein said propagation material comprises said genetic determinant.

13. A propagation material derived from a plant as claimed in claim 1, comprising the genetic determinant.

14. The propagation material as claimed in claim 12 or 13, wherein the propagation material comprises a microspore, pollen, an ovary, an ovule, an embryo, an embryo sac, an egg cell, a cutting, a root, a root tip, a hypocotyl, a cotyledon, a stem, a leaf, a flower, an anther, a seed, a meristematic cell, or a protoplast.

15. A tissue culture of propagation material as claimed in claim 12 or 13.

16. A tissue culture of propagation material as claimed in claim 14.

17. A food product comprising a parthenocarpic fruit or parts thereof as claimed in claim 10, opionally in processed from, wherein said food product comprises said genetic determinant.

18. The pepper plant of claim 1 wherein 10 randomly picked parthenocarpic fruits have an average width of at least about 90% of that of 10 randomly picked seeded fruits of two fruit sets of a plant having the same genetic background.

19. The pepper plant of claim 18 wherein 10 randomly picked parthenocarpic fruits of two fruit sets comply at least with the US Fancy standard classification.

20. The parthenocarpic pepper fruit as claimed in claim 10, wherein the parthenocarpic fruit is at least 95% seedless.

21. The parthenocarpic pepper fruit as claimed in claim 10, wherein the parthenocarpic fruit is at least 98% seedless.

22. The parthenocarpic pepper fruit as claimed in claim 10, wherein the parthenocarpic fruit is at least 99% seedless.

23. The parthenocarpic pepper fruit as claimed in claim 10, wherein the parthenocarpic fruit is 100% seedless.

\* \* \* \* \*